(12) United States Patent
Ishikawa et al.

(10) Patent No.: US 8,875,359 B2
(45) Date of Patent: Nov. 4, 2014

(54) ROTARY DRUM OF FIBER-STACKING DEVICE

(75) Inventors: Shinichi Ishikawa, Kanonji (JP); Tomohiro Fujiwara, Kanonji (JP)

(73) Assignee: Unicharm Corporation, Ehime (JP)

( * ) Notice: Subject to any disclaimer, the term of this patent is extended or adjusted under 35 U.S.C. 154(b) by 50 days.

(21) Appl. No.: 13/824,523

(22) PCT Filed: Sep. 28, 2011

(86) PCT No.: PCT/JP2011/072900
§ 371 (c)(1),
(2), (4) Date: Mar. 18, 2013

(87) PCT Pub. No.: WO2012/043861
PCT Pub. Date: Apr. 5, 2012

(65) Prior Publication Data
US 2013/0276275 A1   Oct. 24, 2013

Related U.S. Application Data

(63) Continuation-in-part of application No. PCT/JP2011/072900, filed on Sep. 28, 2011.

(30) Foreign Application Priority Data

Sep. 30, 2010   (JP) ................. 2010-223037

(51) Int. Cl.
*D04H 5/08* (2012.01)
*D04H 1/736* (2012.01)
*A61F 13/15* (2006.01)
*A61F 13/53* (2006.01)

(52) U.S. Cl.
CPC .............. *D04H 1/736* (2013.01); *D04H 5/08* (2013.01); *A61F 13/15617* (2013.01); *A61F 13/53* (2013.01)
USPC ................ 28/103; 19/148; 19/301; 425/80.1

(58) Field of Classification Search
CPC ........... D04H 1/736; D04H 5/08; D04H 5/10; A61F 13/15658; A61F 13/15617; A61F 13/15707
USPC ........... 28/103, 104, 105, 106, 101, 100, 128, 28/129; 425/80.1, 81.1, 82.1, 83.1; 19/148, 145.7, 301, 296, 304, 308; 264/121, 517
See application file for complete search history.

(56) References Cited

U.S. PATENT DOCUMENTS

| | | | |
|---|---|---|---|
| 4,005,957 A | * | 2/1977 | Savich .................... 425/80.1 |
| 4,592,708 A | * | 6/1986 | Feist et al. .............. 425/80.1 |
| 4,674,966 A | * | 6/1987 | Johnson et al. ........ 425/82.1 |

(Continued)

FOREIGN PATENT DOCUMENTS

| JP | 4-502941 A | 5/1992 |
|---|---|---|
| JP | 2005-534819 A | 11/2005 |

(Continued)

OTHER PUBLICATIONS

International Search Report corresponding to PCT/JP2011/072900, filed Dec. 13, 2011.

*Primary Examiner* — Amy Vanatta
(74) *Attorney, Agent, or Firm* — Lowe Hauptman & Ham, LLP

(57) ABSTRACT

A rotary drum for a fiber-stacking device includes a drum body, pattern plates each having a single fiber-stacking depression, and holding mechanisms each detachably holding a corresponding pattern plate on the outer circumferential surface of the drum body. Each holding mechanism has a fixed hook and a moveable hook. The fixed hook is immovably attached to one side of the drum body and forms a first groove with the drum body. The movable hook is attached to the other side of the drum body to be moveable between a holding position and a release position, forms a second groove with the drum body at the holding position, and opens the second groove at the release position. When the movable hook is at the holding position, the two side parts of the pattern plate are accommodated inside the first and second grooves.

6 Claims, 4 Drawing Sheets

(56) References Cited

U.S. PATENT DOCUMENTS

| | | | | |
|---|---|---|---|---|
| 4,761,258 | A * | 8/1988 | Enloe | 264/518 |
| 4,904,440 | A * | 2/1990 | Angstadt | 264/517 |
| 4,995,141 | A * | 2/1991 | Gould | 19/148 |
| 5,161,283 | A * | 11/1992 | Hansen | 19/148 |
| 5,893,197 | A * | 4/1999 | Vartiainen | 19/301 |
| 6,098,249 | A * | 8/2000 | Toney et al. | 19/296 |
| 6,330,735 | B1 * | 12/2001 | Hahn et al. | 19/296 |
| 6,981,297 | B2 * | 1/2006 | Venturino et al. | 19/296 |
| 7,001,167 | B2 * | 2/2006 | Venturino et al. | 425/80.1 |
| 7,549,853 | B2 * | 6/2009 | Fegelman et al. | 425/80.1 |
| 2005/0261657 | A1 | 11/2005 | Venturino et al. | |

FOREIGN PATENT DOCUMENTS

| | | |
|---|---|---|
| JP | 2007-054219 A | 3/2007 |
| WO | 9005511 A1 | 5/1990 |

* cited by examiner

US 8,875,359 B2

ROTARY DRUM OF FIBER-STACKING DEVICE

RELATED APPLICATIONS

The present application is a National Phase of International Application Number PCT/JP2011/072900, filed Sep. 28, 2011, and claims priority from Japanese Application Number 2010223037, filed Sep. 30, 2010.

TECHNICAL FIELD

The present invention relates to a rotary drum for a fiber-stacking device.

BACKGROUND ART

Known in the art is a rotary drum for a fiber-stacking device which is provided with a drum body and a plurality of pattern plates which respectively have pluralities of fiber-stacking depressions, wherein these pattern plates are attached on the outer circumferential surface of the drum body in a detachable manner (see PLT 1). In this rotary drum, the pattern plates are respectively fastened to the outer circumferential surface of the drum body by pluralities of bolts.

Here, the shapes of the fiber-stacked products are determined by the shapes of the fiber-stacking depressions. Therefore, pattern plates which have fiber-stacking depressions of shapes corresponding to the shapes of the fiber-stacked products to be produced are used. Further, the bottom surfaces of the fiber-stacking depressions have air permeability. For example, when fiber-stacked products should be formed inside the fiber-stacking depressions, a negative pressure is applied to the bottom surfaces of the fiber-stacking depressions. When the fiber-stacked products which are formed in the fiber-stacking depressions should be taken out from the fiber-stacking depressions, positive pressure is applied to the bottom surfaces of the fiber-stacking depressions. Note that, if considering that pattern plates are provided with plate bodies which define the inner circumferential surfaces of the fiber-stacking depressions and bottom plates which define the bottom surfaces of the fiber-stacking depressions, in PLT 1, the plate bodies and the bottom plates are separate from each other.

CITATION LIST

Patent Literature

PLT 1 Japanese Patent Publication (A) No. 2007-54219

SUMMARY OF INVENTION

Technical Problem

When changing the shape of the fiber-stacked product being produced, it is necessary to change the shapes of the fiber-stacking depressions by replacing the pattern plates with other pattern plates. That is, it is necessary to detach the pattern plates from the drum body and reattach other pattern plates to the drum body. Further, when trouble occurs such as clogging of the pattern plates, the pattern plates have to be detached and reattached for replacement or repair.

However, when, like in PLT 1, fastening the pattern plates by bolts, detachment and reattachment of the pattern plates are likely to be troublesome. Further, it is also necessary to prepare a work space for attachment and detachment of bolts.

Solution to Problem

According to the present invention, there is provided a rotary drum for a fiber-stacking device which is provided with: a drum body; a plurality of pattern plates, each of which has at least one fiber-stacking depression; and a plurality of holding mechanisms which hold corresponding pattern plates on an outer circumferential surface of the drum body in a detachable manner, wherein each holding mechanism is provided with: a fixed hook immovably attached to one side of the drum body, the fixed hook forming a fixed side holding groove with the outer circumferential surface of the drum body; and a movable hook attached to the other side of the drum body to be movable between a holding position and a release position, the movable hook forming a movable side holding groove with the outer circumferential surface of the drum body when at the holding position, and opening the movable side holding groove when at the release position, and, wherein when the movable hook is at the holding position, the two side parts of a pattern plate are held in the fixed side holding groove and in the movable side holding groove, whereby the pattern plate is held.

Advantageous Effects of Invention

It is possible to simply detach a pattern plate from the drum body and reattach it to the drum body.

DESCRIPTION OF EMBODIMENTS

Figure 1:
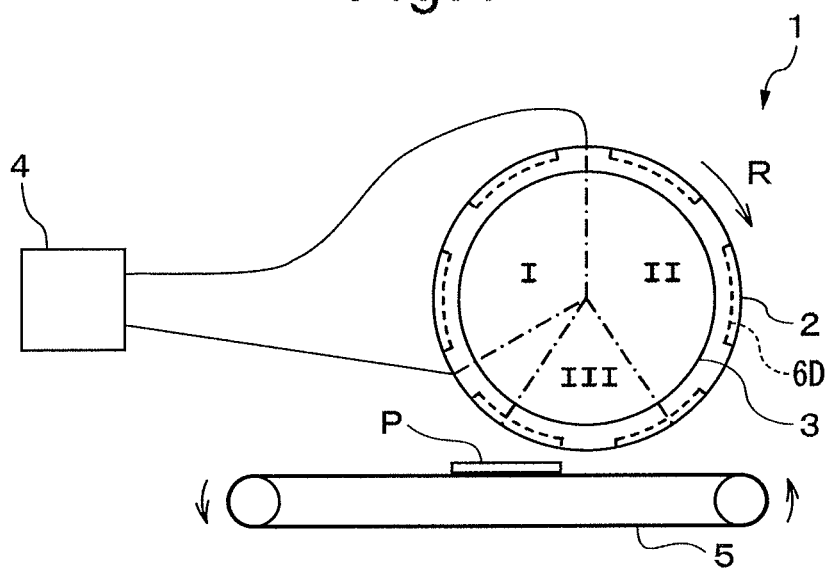
FIG. 1 is a schematic overall view of a fiber-stacking device.

FIG. 1 shows a fiber-stacking device 1 forming part of a system for production of absorbent products. Here, the "absorbent products" include sanitary napkins, panty liners, incontinence pads, and diapers. The fiber-stacked products produced by the fiber-stacking device 1 are used as the absorbent cores of the absorbent products.

Referring to FIG. 1, the fiber-stacking device 1 is provided with a rotary drum 2 which has a plurality of fiber-stacking depressions 6D at its outer circumferential surface, a pressure applying mechanism 3 which applies negative pressure and positive pressure to the rotary drum 2, a feed mechanism 4 which feeds material to the rotary drum 2, and a conveyor mechanism 5 which receives fiber-stacked products from the rotary drum 2 and conveys them out.

In this case, the rotary drum 2 is rotated by a drive mechanism (not shown) in the direction of the arrow R. The pressure applying mechanism 3 applies negative pressure to the fiber-stacking depressions 6D in the regions I and II and applies positive pressure to the fiber-stacking depressions 6D in the region III. The feed mechanism 4 feeds pulp fiber, synthetic fiber, absorbent polymers, and other such materials in a flying state. The conveyor mechanism 5 is for example provided with a belt conveyor.

If fiber material is fed from the feed mechanism 4, the material is sucked into and deposits at the fiber-stacking depressions 6D positioned in the region I, therefore fiber-stacked products P are formed in the fiber-stacking depressions 6D. Next, when the fiber-stacking depressions 6D reach the region III together with the fiber-stacked products P, positive pressure is used so that the fiber-stacked products P are transferred from the fiber-stacking depressions 6D to the conveyor mechanism 5, next, the conveyor mechanism 5 is used to convey them to the next process. Note that, the shapes of the fiber-stacking depressions 6D are determined in accordance with the shape of the fiber-stacked products to be produced.

Figure 2:
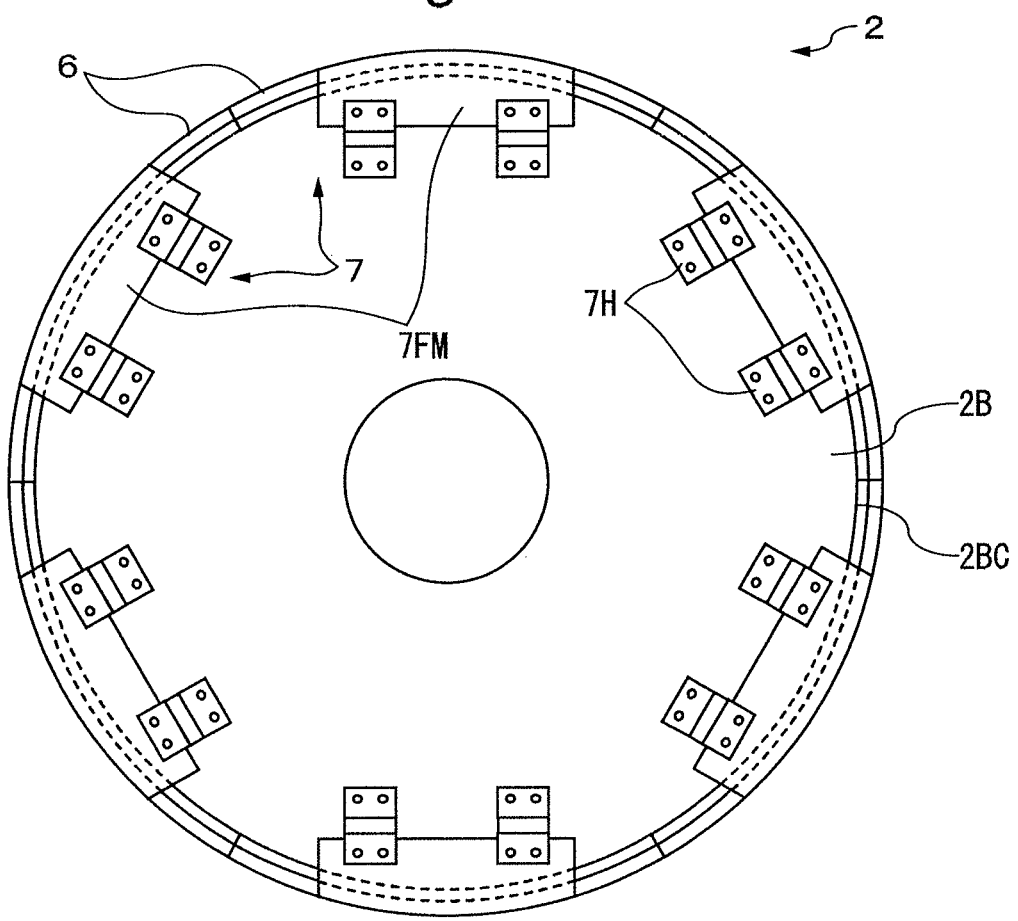
FIG. 2 is a schematic side view of a rotary drum.

Referring to FIG. 2, the rotary drum 2 is provided with a cylindrical drum body 2B, a plurality of pattern plates 6, and a plurality of holding mechanisms 7 which detachably hold the corresponding pattern plates 6 at the outer circumferential surface 2BC of the drum body 2B. In an embodiment of the present invention, six pattern plates 6 and six holding mechanisms 7 are provided.

Figure 3:
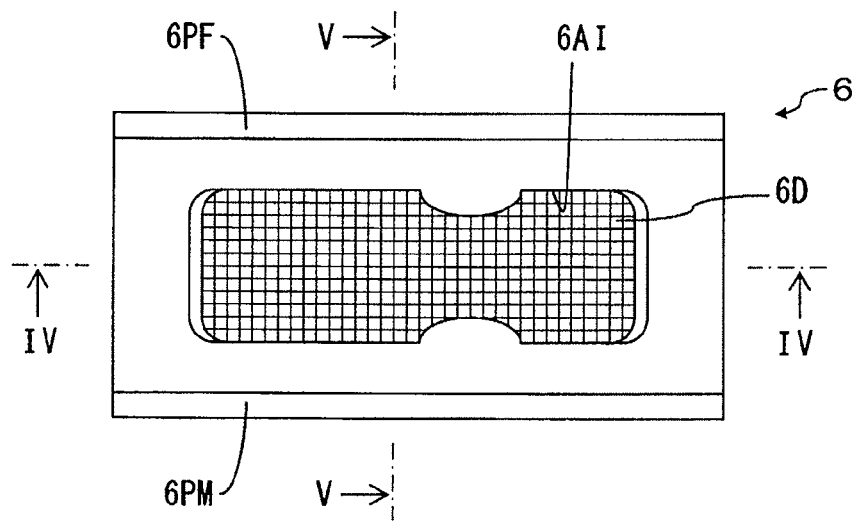
FIG. 3 is a plan view of a pattern plate.
Figure 4:
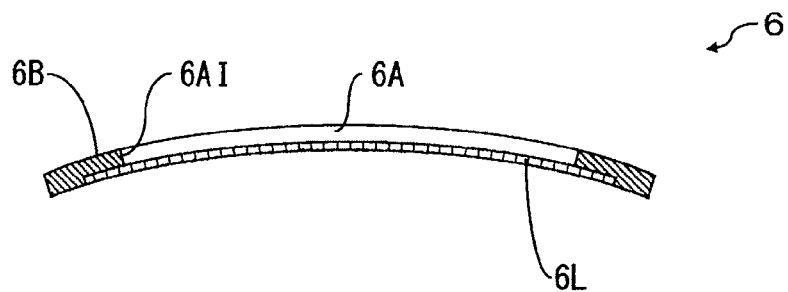
FIG. 4 is a cross-sectional view of a pattern plate seen along a line IV-IV of FIG. 3.
Figure 5:
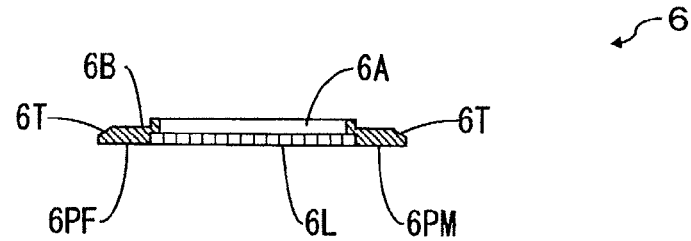
FIG. 5 is a cross-sectional view of a pattern plate seen along a line V-V of FIG. 3.

Referring to FIG. 2, FIG. 3, and FIG. 4, each pattern plate 6 has a single fiber-stacking depression 6D. Note that, each pattern plate 6 may also have a plurality of fiber-stacking depressions 6D. This pattern plate 6 is provided with a plate body 6B which does not have air permeability and with a bottom plate 6L which has air permeability. The bottom plate 6L is for example comprised from a metal mesh and is integrally attached to the bottom surface of the plate body 6B. The plate body 6B has a through hole 6A. The inner circumferential surface 6AI of this through hole 6A defines the inner circumferential surface of the fiber-stacking depression 6D. On the other hand, the bottom plate 6L defines the bottom surface of the fiber-stacking depression 6D.

Further, each pattern plate 6 has projecting parts 6PF and 6PM which project out to the width direction at the two side parts. Further, the top surfaces of the outer edges of the projecting parts 6PF and 6PM are respectively formed with tapered surfaces 6T which expand toward the bottom of the pattern plate 6.

Figure 6:
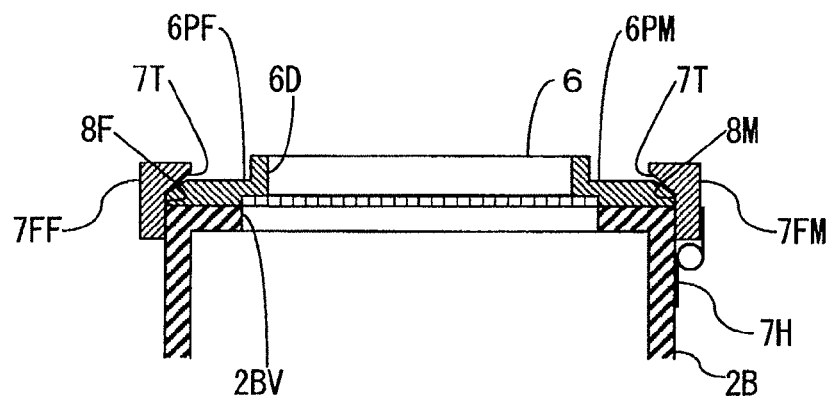
FIG. 6 is a partial cross-sectional view of a rotary drum showing a case when a movable hook is at a holding position.
Figure 7:
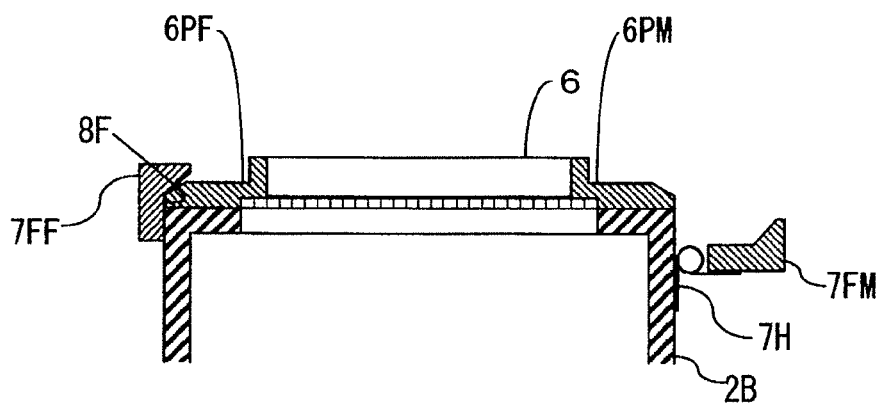
FIG. 7 is a partial cross-sectional view of a rotary drum showing a case when a movable hook is at a release position.

Referring to FIG. 2 while referring to FIG. 6 and FIG. 7, each holding mechanism 7 is provided with a fixed hook 7FF which is attached immovably to one side of the drum body 2B and with a movable hook 7FM which is attached to the other side of the drum body 2B movable between the holding position and the release position. In this case, the movable hook 7 is for example attached through a pair of hinges 7H to the drum body 2B.

FIG. 6 shows the case where a movable hook 7FM is at the holding position, while FIG. 7 shows the case where a movable hook 7FM is at the release position. Note that, in FIG. 6, reference 2BV shows a vent of the drum body 2B. A negative pressure or positive pressure is applied through this vent 2BV to the fiber-stacking depression 6D.

As shown in FIG. 6 and FIG. 7, the fixed hook 7FF extends in part on the outer circumferential surface 2BC of the drum body 2B while curved in the circumferential direction of the drum body 2B. Therefore, a fixed side holding groove 8F is formed between the fixed hook 7FF and the outer circumferential surface 2BC of the drum body 2B.

Further, as shown in FIG. 6, when a movable hook 7FM is at the holding position, the movable hook 7FM extends in part on the outer circumferential surface 2BC of the drum body 2B while curved in the circumferential direction of the drum body 2B. Therefore, a movable side holding groove 8M is formed between the movable hook 7FM and the outer circumferential surface 2BC of the drum body 2B. As opposed to this, when the movable hook 7FM is at the release position, as shown in FIG. 7, the movable hook 7FM does not extend on the outer circumferential surface 2BC of the drum body 2B. Therefore, when the movable hook 7FM is at the release position, the movable side holding groove 8M is open or is not formed. Note that, in this embodiment of the present invention, the lengths of the fixed hook 7FF and movable hook 7FM in the circumferential direction of the drum body 2B are shorter than the length of the pattern plate 6 in the circumferential direction.

Furthermore, the surface of the fixed hook 7FF defining the inner surface of the fixed side holding groove 8F and the surface of the movable hook 7FM defining the inner surface of the movable side holding groove 8M are respectively formed with tapered surfaces T expanding toward the pattern plate 6.

Now, when attaching a pattern plate 6 to the drum body 2B, first, the movable hook 7FM is positioned at the open position shown in FIG. 7. Next, the projecting part 6PF of the pattern plate 6 is inserted and held in the fixed side holding groove 8F. In this case, the projecting part 6PF and the fixed hook 7FF are formed with tapered surfaces 6T and 7T, so insertion of the projecting part 6PF becomes easy.

Next, the movable hook 7FM is moved to the holding position shown in FIG. 6. As a result, the projecting part 6PM of the pattern plate 6 is accommodated in the movable side holding groove 8M. In this way, the two side parts of the pattern plate 6 are accommodated in the fixed side holding groove 8F and movable side holding groove 8M, whereby the pattern plate 6 is held on the outer circumferential surface 2BC of the drum body 2B.

Here, in an embodiment according to the present invention, the fixed hook 7FF and the movable hook 7FM are formed so that when the movable hook 7FM is moved from the open position to the holding position, the movable hook 7FM abuts against the pattern plate 6 and, due to this, the projecting part 6PF is pushed into the fixed side holding groove 8F. As a result, it is possible to reliably hold the pattern plate 6 by a simple method.

Further, in this case, the tapered surface 6T of the projecting part 6PF and the tapered surface 7T of the fixed hook 7FF abut against each other, while the tapered surface 6T of the projecting part 6PM and the tapered surface 7T of the movable hook 7FM abut against each other. As a result, due to the fixed hook 7FF and movable hook 7FM, the pattern plate 6 is pushed against the outer circumferential surface 2BC of the drum body 2. Therefore, it is possible to reliably hold the pattern plate 6. Further, it is possible to suppress leakage between the pattern plate 6 and the drum body 2B.

When the rotary drum 2 is rotated, a centrifugal force acts on each pattern plate 6. However, even in this case, the projecting parts 6PF and 6PM of the pattern plate 6 are held inside the fixed side holding groove 8F and movable side holding groove 8M, so it is possible to reliably hold the pattern plate 6 at the drum body 2B.

On the other hand, when detaching a pattern plate 6 from the drum body 2B, the movable hook 7FM is moved to the open position shown in FIG. 7. As a result, the projecting part 6PM is released from the movable hook 7FM or the holding mechanism 7. Therefore, it becomes possible to detach the pattern plate 6 from the drum body 2B. In this way, it is possible to simply detach the pattern plate 6 from the drum body 2B.

Furthermore, in an embodiment according to the present invention, each pattern plate 6 has a single fiber-stacking depression 6D. Therefore, when some trouble occurs in one fiber-stacking depression 6D, it is sufficient to detach one pattern plate 6 from the drum body 2B. Therefore, replacement or maintenance of pattern plates 6 becomes easier.

Further, the plate body 6B and the bottom plate 6L are integrally formed. Therefore, detachment and reattachment of a pattern plate 6 become easier.

Figure 8:
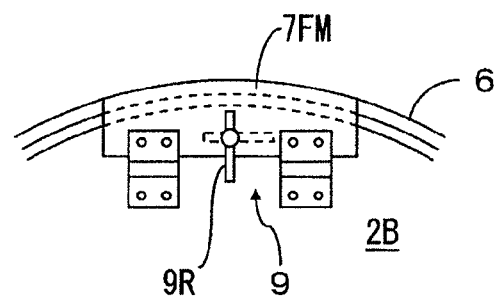
FIG. 8 is a schematic view of a locking mechanism.

FIG. 8 shows the case of a holding mechanism 7 being provided with a locking mechanism 9 for releasably locking the movable hook 7FM at the holding position. This locking mechanism 9 is provided with a locking rod 9R which can move between a locking position shown by the solid line in FIG. 8 and an unlocked position shown by the broken line in FIG. 8.

When the locking rod 9R is positioned at the locking position, the locking rod 9R engages with the drum body 2B, for example, therefore the movable hook 7FM is prevented from moving from the holding position. When the locking rod 9R is positioned at the unlocking position, the locking rod 9R no longer engages with the drum body 2B, therefore the movable hook 7FM can move to the open position. If providing the locking mechanism 9 in this way, it is possible to reliably maintain the movable hook 7FM at the holding position and, therefore, possible to reliably maintain the pattern plate 6 on the drum body 2B.

Figure 9:
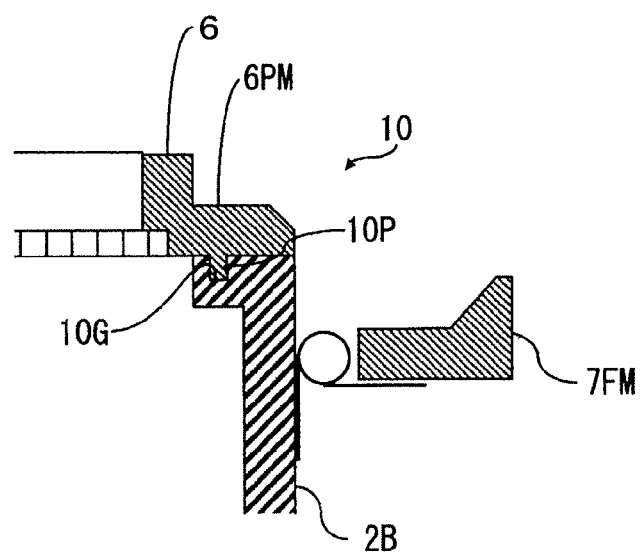
FIG. 9 is a schematic view of a temporary fastening mechanism.

FIG. 9 shows the case where the rotary drum 2 is provided with a temporary fastening mechanism 10 for temporarily fastening a pattern plate 6 to the drum body 2B. The temporary fastening mechanism 10, for example, is provided with a pin 102 and a receiving groove 10G which receives the pin 102. In the example shown in FIG. 9, the pin 10P is formed at the pattern plate 6, while the receiving groove 10G is formed at the drum body 2B. Note that, it is also possible to provide the receiving groove 10G at the pattern plate 6 and provide the pin 102 at the drum body 2B.

When attaching a pattern plate 6 at the drum body 2B, the projecting part 6PF of the pattern plate 6 is accommodated in the fixed side holding groove 8F, then the pin 10 is accommodated in the receiving groove 10G. As a result, even when the movable hook 7FM is at the release position, the pattern plate 6 can be held at the targeted position. Further, positioning of the pattern plate 6 becomes easy. Note that, if considering ease detachment and reattachment of the pattern plate 6, the inside diameter of the receiving groove 10G is preferably slightly larger than the diameter of the pin 10P.

REFERENCE SIGNS LIST

1 fiber-stacking device
2 rotary drum
2B drum body
2BC outer circumferential surface of drum body
6 pattern plate
6D fiber-stacking depressions
6B plate body
6L bottom plate
6PF, 6PM projecting parts
6T taper surface
7 holding mechanism
7FF fixed hook
7FM movable hook
8F fixed side holding groove
8M movable side holding groove
9 locking mechanism
10 temporary fastening mechanism
P fiber-stacked products

The invention claimed is:

1. A rotary drum for a fiber-stacking device which is provided with:
   a drum body;
   a plurality of pattern plates, each of which has at least one fiber-stacking depression; and
   a plurality of holding mechanisms which hold corresponding pattern plates on an outer circumferential surface of the drum body in a detachable manner,
   wherein each holding mechanism is provided with:
      a fixed hook immovably attached to one side of the drum body, the fixed hook forming a fixed side holding groove with the outer circumferential surface of the drum body; and
      a movable hook attached to the other side of the drum body to be movable between a holding position and a release position, the movable hook forming a movable side holding groove with the outer circumferential surface of the drum body when at the holding position, and opening the movable side holding groove when at the release position, and,
   wherein when the movable hook is at the holding position, the two side parts of a pattern plate are held in the fixed side holding groove and in the movable side holding groove, whereby the pattern plate is held.

2. A rotary drum as set forth in claim 1, wherein the pattern plate is provided with a plate body which defines the inner circumferential surface of a fiber-stacking depression and a bottom plate which defines a bottom surface of the fiber-stacking depression, and wherein these plate body and bottom plate are integrally formed.

3. A rotary drum as set forth in claim 1, wherein each pattern plate has a single fiber-stacking depression.

4. A rotary drum as set forth in claim 1, wherein the fixed hook and movable hook are formed so that when the movable hook is moved from the release position to the holding position, the movable hook pushes a corresponding side part of the pattern plate into the fixed side holding groove.

5. A rotary drum as set forth in claim 1, wherein a surface of the fixed hook which defines an inner surface of the fixed side holding groove and a surface of the movable hook which defines an inner surface of the movable side holding groove are respectively formed with tapered surfaces expanding toward the corresponding pattern plate, outer edges of the two side parts of the pattern plate are respectively formed with tapered surfaces expanding toward a bottom of the pattern plate, and these tapered surfaces abut against each other.

6. A rotary drum as set forth in claim 1, wherein the holding mechanism is further provided with a locking mechanism for locking the movable hook at the holding position in a reversible manner.

* * * * *